United States Patent [19]

Gregory et al.

[11] Patent Number: 4,531,014

[45] Date of Patent: Jul. 23, 1985

[54] PROCESS FOR THE CONVERSION OF A $C_2$ TO $C_{10}$ ALIPHATIC LINEAR OLEFIN TO A PRODUCT COMPRISING HYDROCARBONS OF HIGHER CARBON NUMBER

[75] Inventors: Reginald Gregory, Camberley; David J. Westlake, Woking, both of England

[73] Assignee: The British Petroleum Company p.l.c., London, England

[21] Appl. No.: 577,842

[22] Filed: Feb. 7, 1984

[30] Foreign Application Priority Data

Feb. 10, 1983 [GB] United Kingdom ................ 8303740

[51] Int. Cl.$^3$ .............................................. C07C 3/10
[52] U.S. Cl. .................................... 585/415; 502/72; 502/81; 502/84; 585/407; 585/520; 585/530; 585/533
[58] Field of Search ..................... 502/81, 82, 83, 84, 502/72; 585/415, 407, 520, 530, 533

[56] References Cited

U.S. PATENT DOCUMENTS

| | | | |
|---|---|---|---|
| 3,412,039 | 11/1968 | Miller | 502/81 |
| 3,432,571 | 3/1969 | Noddings et al. | 502/84 |
| 3,459,815 | 8/1969 | Noddings et al. | 502/83 |
| 3,845,150 | 10/1974 | Yan et al. | 585/415 |
| 4,153,638 | 5/1979 | Bercik et al. | 585/533 |
| 4,299,730 | 11/1981 | Sommer et al. | 502/81 |
| 4,329,257 | 5/1982 | Sommer et al. | 502/83 |
| 4,456,779 | 6/1984 | Owen et al. | 585/315 |

*Primary Examiner*—D. E. Gantz
*Assistant Examiner*—A. Pal
*Attorney, Agent, or Firm*—Brooks, Haidt, Haffner & Delahunty

[57] ABSTRACT

$C_2$ to $C_{10}$, preferably $C_3$ to $C_6$, aliphatic linear olefins are converted to a product comprising at least one hydrocarbon of higher carbon number selected from dimers, oligomers, alkanes, olefins and aromatics by contacting the olefin at elevated temperature with a catalyst comprising a cation-exchangeable layered clay.

19 Claims, No Drawings

PROCESS FOR THE CONVERSION OF A $C_2$ TO $C_{10}$ ALIPHATIC LINEAR OLEFIN TO A PRODUCT COMPRISING HYDROCARBONS OF HIGHER CARBON NUMBER

The present invention relates in general to a process for the conversion of a $C_2$ to $C_{10}$ aliphatic linear olefin to a product comprising hydrocarbons of higher carbon number including one or more of dimers, oligomers, alkanes, olefins and aromatics.

Low molecular weight polymers of propylene and butylene, and in particular butylene, are manufactured and used on a large scale. The polybutenes, for example, are clear, tasteless, nontoxic, tacky and very viscous liquids with a viscosity that is not highly temperature dependent, and are typically used in adhesives, caulking compounds, sealants, and coatings, or as additives for internal combustion engine oil, and plasticisers for plastics and resins. Propylene oligomers, and in particular the tetramer, are used extensively in the production of lubricating oil additives. Aromatics are widely used as solvents and detergents precursors.

Hydrocarbon mixtures of the aforesaid composition have been proposed as gasoline blending components.

Generally, low molecular weight, lower olefin polymers are produced by either strong acid or Friedel-Crafts catalysed polymerisation. Polybutenes, for example, are produced by continuously feeding a refinery butane/butene stream containing butanes, isobutylene, butenes and minor concentrations of $C_3$ and $C_5$ hydrocarbons into a reactor containing aluminium chloride as catalyst. Polyisobutylene, as distinct from polybutylenes, is prepared in a similar manner using purified isobutylene as feed. It is not uncommon to use cocatalysts such as aluminium and/or titanium alkyls. Another commercial process produces oligomers and cooligomers selectively from propylene and butenes using supported phosphoric acid as catalyst.

It is also known to oligomerise certain olefins using clays as catalysts. Thus U.S. Pat. No. 3,432,571 describes the dimerisation and removal of tertiary olefins containing 4 to 5 carbon atoms per molecule from admixture with normal olefins by passing the gaseous mixture over montmorillonite clay exchanged after acid activation with chromium or phosphorus in the absence of water to effect the dimerisation of the tertiary olefins to produce a stream lean in tertiary olefins. U.S. Pat. No. 3,213,037 describes the polymerisation of isobutylene dimer using as catalyst an acid treated bentonite. Finally, EP-A-14765 describes the manufacture of 1-phenyl-1,3,3-trimethylindan by dimerisation of alpha-methylstyrene using an acid treated bentonite. The olefin feed in the processes described in the aforesaid patent specifications are acknowledged as being susceptible to dimerisation or oligomerisation. Aliphatic linear olefins having from 2 to 10 carbon atoms on the other hand are recognised by those skilled in the art to be very much less susceptible to dimerisation or oligomerisation, otherwise a process such as that described in U.S. Pat. No. 3,432,571 would not be effective.

We have now found to our surprise that aliphatic linear $C_2$ to $C_{10}$ olefins can be converted using a specific type of clay catalyst to a product comprising hydrocarbons of higher carbon number including one or more of dimers, oligomers, alkanes, olefins and aromatics, which product could have application as a high octane gasoline blending component.

Accordingly the present invention provides a process for the conversion of a $C_2$ to $C_{10}$ aliphatic linear olefin to a product comprising hydrocarbons of higher carbon number including one or more of dimers, oligomers, alkanes, olefins and aromatics which process comprises contacting the olefin at elevated temperature with a catalyst comprising a cation-exchangeable layered clay.

Throughout this specification the term "layered clay" means a clay having a lamellar structure with interlamellar spaces disposed between the lamellar layers and includes such clays which have been modified by the inclusion therein of pillars, and which are sometimes referred to as stabilised pillared layered clays or simply as pillared layered clays, or in other ways which do not destroy to any appreciable extent their layered structure.

The unmodified clay may be a natural or synthetic layered clay. Of the many types of layered clay available (see for example "Encyclopedia of Chemical Technology [Kirk Othmer], 3rd Edition, published by John Wiley and Sons, pages 190–206), it is preferred to use the smectite class of layered clays. Both dioctahedral and trioctahedral smectite-type clays may be employed. Examples of suitable layered clays include montmorillonite, bentonite, beidellite, nontronite and hectorite, of which montmorillonite or bentonite is preferred. The nomenclature of clay minerals has undergone revision over the years but in the present specification bentonite includes minerals, such as Wyoming bentonite, containing a substantial proportion of montmorillonite. An example of a suitable synthetic smectite-type layered clay and a method for its preparation is described in U.S. Pat. No. 3,855,147.

The clays in their natural state normally contain exchangeable sodium or calcium ions in the interlamellar space. Such clays have some catalytic activity in the process of the present invention. In order to bestow increased catalytic activity on the clay it is necessary to exchange some of all of the exchangeable metal cations with one or more other suitable cations.

The $Ca^{2+}$ or $Na^+$ cations normally associated with layered clays may suitably be exchanged with either hydrogen ions or cations of the metals chromium, aluminium, gallium, cobalt, nickel, iron, copper or vanadium. Preferably the layered clays are exchanged with either hydrogen ions, and/or aluminium ions.

Cation-exchange of smectite-type layered clays may be effected by any technique which essentially preserves the layered structure of the clay. A general discussion of the factors affecting cation-exchange may be found in European patent publication Nos. 0031252 and 0031687 to which the reader is referred for further details. With regard to the smectite-type hydrogen-exchanged clay for example, hydrogen ion-exchange is preferably effected by contacting the clay containing exchangeable cations with a solution containing an acid under ion-exchange conditions. Preferably the solution of the acid is an aqueous solution. Suitable acids are mineral acids, including sulphuric and hydrochloric acid, but other acids, such as carboxylic acids may be used if so desired. The acid may suitably be from 0.5 to 10 molar, although lower concentrations may be used. Although contact of the clay with the mineral acid is preferably effected at or near ambient temperature, elevated temperatures which do not destroy the layered structure and the catalytic activity of the clay may be employed, eg up to about 35° C. The period of contact will depend to some extent on the temperature. Typically, at ambient temperature the contact period may be in the range from ¼ hour to 3 days, preferably ¼ hour to 1 day.

Techniques for separating the cation-exchanged layered clay from the ion-exchange media and excess ions are well known. Any suitable solid/liquid separation procedure can be used. Decantation and centrifugation are two preferred methods for solid/liquid separation.

After exchange the cation-exchanged layered clays are preferably washed until all extraneous metal cations are removed. Thereafter the clay is preferably dried. Although drying is preferably effected at elevated temperature, temperatures which cause collapse of the layered structure must be avoided. Generally, for cation-exchanged smectites drying temperatures in the range 20° to 120° C. are suitable. The clays may suitably be activated before use as catalysts by heating in air at a temperature which does not collapse the layered structure, suitably up to 180° C., preferably from 80° to 150° C. for hydrogen exchanged smectites; suitably up to about 200° C., preferably from 80° to 200° C. for metal cation-exchanged clays. The catalyst may suitably be combined with other compounds, for example silica, in order to aid pellet or particle stability.

Suitable stabilised pillared interlayered clays which may be used in the process of the invention and methods for making them are described in the specifications of U.S. Pat. Nos. 4,176,090, 4,216,188 4,271,043 and 4,248,739. Typically, the pillared clays may be prepared by reacting a colloidal solution of a mono-ionic montmorillonite having a concentration of 100 mg to 800 mg montmorillonite per liter, in the form of fully dispersed negatively charged unit layers at room temperature with an aged sol of a metal hydroxide aged for at least 5 days at ambient temperature, said metal hydroxide being selected from the group consisting of aluminium hydroxide and chromium hydroxide, at a pH adjusted below the zero charge point having a residual net positive charge on the said metal hydroxide, under vigorous agitation, resulting in a rapid flocculation of the montmorillonite cross-linked with said metal hydroxide, separating the product from the liquid phase, and stabilising the product by heat treatment. Further details of this process may be found in U.S. Pat. No. 4,216,188. Alternatively, the pillared clays may suitably be prepared by reacting a smectite-type clay, such as montmorillonite, with an aqueous solution of a polymeric cationic hydroxy inorganic metal complex, such as chlorhydrol. Further details of this method may be found in U.S. Pat. No. 4,248,739.

The pillared clays may suitably be modified by cation-exchange following treatment with an inorganic base, for example potassium hydroxide or ammonia. A suitable process is described in U.S. Pat. No. 4,248,739 for example, to which the reader is referred for further details.

Alternatively, the catalyst may be a stabilised pillared interlayered clay in which the pillars are formed after exchanging the natural cations of the clay with more suitable cations, as hereinbefore described. The preparation of stabilised pillared interlayered clays according to this procedure is described in, for example, U.S. Pat. No. 4,238,364.

The olefin to be converted is a $C_2$ to $C_{10}$, preferably a $C_3$ to $C_6$, aliphatic linear olefin, for example propylene, but-1-ene, 4-methylpent-1-ene, pent-1-ene, hex-1-ene and hex-2-ene. For the avoidance of doubt, olefins di-substituted at the olefinic carbon, for example isobutene, and tertiary olefins and alpha-methylstyrene are not regarded as aliphatic linear olefins for the purpose of the present invention. As an alternative to feeding individual $C_2$ to $C_{10}$ linear olefins, mixtures of the aforesaid olefins may be employed. Furthermore, the $C_2$ to $C_{10}$ aliphatic linear olefins may be admixed with olefins other than $C_2$ to $C_{10}$ linear olefins, for example branched olefins.

The process may be operated in the liquid phase or in the vapour phase or in a mixed liquid/vapour phase and in the presence or absence of a solvent. For example, using high-boiling normally liquid olefins, the process may be operated in the absence of a solvent. In the case of lower-boiling normally gaseous olefins such as propylene a solvent may be used to provide an essentially liquid or mixed vapour/liquid phase under the reaction conditions. Suitably the solvent may be a normally liquid hydrocarbon, for example n-heptane.

A suitable feedstock is a hydrocarbon mixture comprising olefins and paraffins as found in petroleum refinery streams, such as those derived from steam or catalytic cracking of petroleum fractions.

The process may be operated at atmospheric or at a superatmospheric pressure, preferably at a pressure sufficient to produce at least in part a liquid phase. The process may suitably be operated at a temperature in the range from 50° to 550° C., preferably from 50° to 450° C.

The actual temperature employed is a factor in determining the nature of the product distribution. As one component of the product there is formed dimers and oligomers of the formula (olefin)$_n$ where n may be in the range 2 to about 6 and especially 2 to 4, for example butene dimers and trimers and propylene trimers and tetramers. Using a mixture of olefins, co-dimers and/or co-oligomers may be produced. Dimers and/or oligomers are generally formed to a greater or lesser extent over the whole of the aforesaid temperature range. Other components of the product can include alkanes and olefins (including diolefins) which may be predominantly branched and surprisingly can have a range of carbon numbers which are not simple muliples of the carbon number of the feed olefin or olefins and aromatics which may contain up to 18 or more carbon atoms. At higher temperatures in the aforesaid range the product contains greater proportions of alkanes and aromatics than at the lower temperatures. Generally, substantial amounts of hydrocarbons other than oligomers may be obtained at temperatures above 150° C., preferably above 200° C. and below 450° C.

The process may be operated batchwise or continuously preferably continuously.

The hydrocarbon components of the product may be recovered or separated into suitable fractions by conventional means, for example by fractional distillation. Mixtures of some or all of the hydrocarbon components or fractions may be used as gasoline blending components.

The invention will now be further illustrated by reference to the following Examples.

PREPARATION OF CATION-EXCHANGED LAYERED CLAYS AND STABILISED PILLARED LAYERED CLAYS

Hydrogen Ion-Exchanged Wyoming Bentonite (A)

Sodium bentonite (a Wyoming Bentonite supplied as a fine powder for use in drilling muds) was added to a solution of concentrated sulphuric acid (400 ml) in water (1100 ml) and left at room temperature for 2 days with occasional stirring. The clay was separated from the solution and washed with water by repeated centrifuging and resuspending in water until the pH of the supernatant solution was the same as the distilled water used in the washing. The clay was dried at 80° C. in air and ground to give a fine powder (for batch reactions) or granules (for continuous reactions) of hydrogen bentonite.

Aluminium Ion-Exchanged Wyoming Bentonite (B)

Wyoming bentonite powder (100 g) was added to a solution of aluminium sulphate [$Al_2(SO_4)_3.16H_2O$] (250 g) in distilled water (1.5 liter) and left overnight. The clay was centrifuged, mixed with a further 1.5 liters of water and recentrifuged. This was repeated a second time to remove all extraneous ions. Finally, the aluminium ion-exchanged clay was oven dried at 80° C.

Alumina Pillared Wyoming Bentonite (C)

Wyoming bentonite (600 g) was added into the vortex of a well stirred solution of chlorhydrol (600 g of 50% aqueous solution) in 12 liters of deionised water. The pH of the solution was adjusted to 5.5 by adding dilute ammonia solution. The vigorously stirred solution was then heated at 65° C. for one hour whilst the pH was maintained at 5.5 by further additions of ammonia solution. On cooling to room temperature, the clay was centrifuged, added to a further 12 liters of deionised water, stirred and recentrifuged, and washed until free of all extraneous ions. The alumina pillared Wyoming bentonite was made by drying the clay at 80° C., then heat treating at 400° C. for 4 hours. The alumina pillared Wyoming bentonite showed a strong $d_{001}$ absorption band at 17.9 Å in its X-ray diffraction spectrum.

Hydrogen Ion-Exchanged Alumina Pillared Wyoming Bentonite (D)

The alumina pillared Wyoming bentonite (C), previously heat treated at 400° C. for 4 hours in air was ground to granules of 1–2 mm, immersed in a 1M solution of potassium hydroxide solution and left overnight. The granules were filtered on a sintered glass funnel and washed with water until all extraneous ions were removed. The granules were then immersed in a dilute sulphuric acid solution, prepared by mixing 100 ml of concentrated sulphuric acid and 500 ml deionised water, and left overnight. The granules were filtered on a sintered glass funnel, washed with water until free of all extraneous ions, and dried at 80° C. in air. The granules of hydrogen ion-exchanged alumina pillared Wyoming bentonite so prepared had a very strong X-ray diffraction absorption at 16.0 Å corresponding to the $d_{001}$ spacing.

Aluminium Ion-Exchanged Alumina Pillared Wyoming Bentonite (E)

A similar preparation to that for hydrogen ion-exchanged alumina pillared Wyoming bentonite (C), except that the dilute sulphuric acid solution was replaced by a 1M solution of aluminium chloride, was carried out. The granules of aluminium ion-exchanged alumina pillared Wyoming bentonite showed a strong X-ray diffraction $d_{001}$ absorption at 17.2 Å.

EXAMPLE 1

Propene (50 ml, 26 g) was charged into a stainless steel autoclave (volume 200 ml) containing hydrogen ion-exchanged Wyoming bentonite (A) (5 g). The autoclave was sealed and stirred, by means of a sealed magnetic driven stirrer, at a reaction temperature of 85° C. for a reaction period of 2.5 hours. On cooling, the gaseous products were vented off, and the liquid and solid products removed. The solid was filtered off, and the liquid product was weighed and analysed by field ionisation mass spectrometry using a MS50 mass spectrometer and an ion source developed by Kratos limited. The experimental results are based on relative molecular ion intensities and exclude unconverted reactant or solvent present in the product.

EXAMPLE 2

Example 1 was repeated but at a reaction temperature of 100° C. instead of 85° C.

EXAMPLE 3

Example 1 was repeated but at a reaction temperature of 150° C. instead of 85° C.

EXAMPLE 4

Example 1 was repeated but at a reaction temperature of 200° C. instead of 85° C.

The results of Examples 1 to 4 are shown in Table 1.

EXAMPLE 5

Example 1 was repeated but propene (20 ml, 10.4 g) was charged into the autoclave containing the hydrogen ion-exchanged Wyoming bentonite (A) (5 g) and heptane (50 g). The reaction mixture was heated at a reaction temperature of 100° C. for a reaction period of 2.5 hours.

EXAMPLE 6

Example 5 was repeated but at a reaction temperature of 150° C. instead of 100° C.

EXAMPLE 7

Example 5 was repeated but at a reaction temperature of 200° C. instead of 100° C.

EXAMPLE 8

Example 5 was repeated but at a reaction temperature of 230° C. instead of 100° C.

EXAMPLE 9

Example 8 was repeated but the hydrogen ion-exchanged Wyoming bentonite (A) (5 g) was replaced by the aluminium ion-exchanged Wyoming bentonite (B) (5 g).

The results of Examples 5 to 9 are shown in Table 2.

TABLE 1

| Example No | Wt of Liquid Products/ Wt of Reactant Propene | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 1 | 0.10 | 143 | 7 | 82 | 8 | 3 |
| 2 | 0.23 | 142 | 8 | 80 | 10 | 2 |
| 3 | 0.60 | 139 | 13 | 66 | 15 | 6 |
| 4 | 0.91 | 170 | 17 | 50 | 19 | 14 |

TABLE 2

| Example No | Wt of Liquid Product/ Wt of Reactant Propene | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 5 | 0.24 | 98 | 3 | 86 | 1 | 10 |
| 6 | 0.74 | 118 | 1 | 81 | 9 | 9 |
| 7 | 1.00 | 138 | 17 | 60 | 12 | 11 |
| 8 | 1.00 | 135 | — | 48 | 10 | 42 |
| 9 | 1.00 | 116 | 17 | 49 | 6 | 28 |

EXAMPLE 10

Example 1 was repeated but the propene was replaced by but-1-ene (50 ml, 29.8 g) and the reaction temperature was 100° C. instead of 85° C.

EXAMPLE 11

Example 10 was repeated but at a reaction temperature of 150° C. instead of 100° C.

EXAMPLE 12

Example 10 was repeated but a reaction temperature of 200° C. instead of 100° C.

EXAMPLE 13

Example 12 was repeated but using hydrogen ion-exchanged alumina pillared Wyoming bentonite (D) (5 g) instead of hydrogen ion-exchanged Wyoming bentonite (A).

EXAMPLE 14

Example 11 was repeated but using aluminium ion-exchanged alumina pillared Wyoming bentonite (E) (5 g) instead of hydrogen ion-exchanged Wyoming bentonite (A).

The results of Examples 10 to 14 are shown in Table 3.

EXAMPLE 15

Example 10 was repeated but but-1-ene (25 ml, 14.9 g) was charged into the autoclave containing hydrogen ion-exchanged Wyoming bentonite (A) (5 g) and heptane (50 g). The reaction mixture was heated at a reaction temperature of 150° C. for a period of 2.5 hours.

EXAMPLE 16

Example 15 was repeated but at a reaction temperature of 200° C. instead of 150° C.

The results of Examples 15 and 16 are shown in Table 4.

TABLE 3

| Example No | Wt of Liquid Products/ Wt of Reactant Butene | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 10 | 0.40 | 117 | 9 | 80 | 10 | 1 |
| 11 | 0.70 | 116 | 9 | 78 | 12 | 1 |
| 12 | 1.00 | 169 | 16 | 51 | 20 | 13 |
| 13 | 0.65 | 100 | 10 | 79 | 11 | — |
| 14 | 0.66 | 109 | 12 | 76 | 12 | — |

TABLE 4

| Example No | Wt of Liquid Product/ Wt of Reactant But-1-ene | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 15 | 0.20 | 108 | — | 100 | — | — |
| 16 | 0.85 | 131 | — | 82 | 18 | — |

EXAMPLE 17

Example 19 was repeated but the but-1-ene was replaced by 4-methylpent-1-ene (20 g). The 4-methylpent-1-ene was added to the autoclave as a liquid before sealing.

EXAMPLE 18

Example 17 was repeated but the 4-methylpent-1-ene was replaced by 2-methylpent-1-ene (20 g).

EXAMPLE 19

Example 17 was repeated but the 4-methylpent-1-ene was replaced by hex-1-ene (20 g).

EXAMPLE 20

Example 17 was repeated but the 4-methylpent-1-ene was replaced by hex-2-ene (20 g).

EXAMPLE 21

Example 18 was repeated but in the absence of heptane.

The results of Examples 17 to 21 are shown in Table 5.

EXAMPLE 22

Example 11 was repeated but with the further addition of hex-1-ene (50 ml, 33.6 g). The result is shown in Table 6. The alkenes in the liquid products contained a major amount of a $C_{10}$ alkene formed by the co-dimerisation of but-1-ene and hex-1-ene.

EXAMPLE 23

Example 22 was repeated but at a reaction temperature of 200° C. instead of 150° C. The result is shown in Table 6. The alkenes in the liquid product contained major amounts of a $C_{10}$ alkene formed by the co-dimerisation of but-1-ene and hex-1-ene, and a $C_{14}$ alkene formed by the co-oligomerisation of two but-1-ene molecules and one hex-1-ene molecule.

TABLE 5

| Example No | Hexene Conversion to Other Than Hexene Isomers (% w/w) | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 17 | 51 | 160 | — | 78 | 22 | — |
| 18 | 17 | 147 | 20 | 31 | 25 | 24 |
| 19 | 34 | 160 | — | 71 | 12 | 17 |
| 20 | 22 | 167 | — | 73 | 5 | 22 |
| 21 | 0.73 | 163 | 20 | 31 | 25 | 24 |

TABLE 6

| Example No | Hexene Conversion to Other Than Hexene Isomers (% w/w) | Average Molecular Wt of Liquid Products | Approximate Composition of Liquid Products % Wt | | | |
|---|---|---|---|---|---|---|
| | | | Alkanes | Alkenes | Di- and Tri-Alkenes | Aromatics |
| 22 | 15 | 139 | 11 | 82 | 7 | — |
| 23 | 65 | 165 | 12 | 67 | 16 | 5 |

We claim:

1. A process for the conversion of a $C_2$ to $C_{10}$ aliphatic linear olefin to a product comprising at least one hydrocarbon of higher carbon number selected from dimers, oligomers, alkanes, olefins and aromatics which process comprises contacting the olefin at elevated temperature with a catalyst comprising a cation-exchangeable layered clay, selected from the group consisting of a naturally occurring smectite-type clay and a stabilised pillared smectite-type clay.

2. A process according to claim 1 wherein the layered clay is selected from montmorillonite and bentonite.

3. A process according to claim 1 wherein the layered clay is a stabilised pillared interlayered clay.

4. A process according to claim 1 wherein the layered clay is exchanged with a cation selected from hydrogen and aluminium.

5. A process according to claim 1 wherein the olefin is a $C_3$ to $C_6$ aliphatic linear olefin.

6. A process according to claim 1 wherein a mixture of olefins is employed.

7. A process according to claim 6 wherein the mixture of olefins is derived from steam or catalytic cracking of petroleum fractions.

8. A process according to claim 1 when operated at a temperature in the range from 50° to 550° C.

9. A process according to claim 1 when operated at a temperature in the range 200° to 450° C.

10. A process for the conversion of an aliphatic linear olefin selected from the group consisting of (a) a $C_6$ to $C_{10}$ aliphatic linear olefin and (b) a mixture of a $C_6$ to $C_{10}$ aliphatic linear olefin with a $C_2$ to $C_5$ aliphatic linear olefin, to a product comprising at least one hydrocarbon of higher carbon number selected from dimers, oligomers, alkanes, olefins and aromatics which process comprises contacting the olefin at elevated temperature with a catalyst comprising a cation-exchangeable layered clay selected from the group consisting of a naturally occurring smectite type clay and a stabilised pillared interlayered clay thereof, said layered clay having been exchanged with a cation selected from the group consisting of hydrogen and aluminium.

11. The process according to claim 10,
wherein the aliphatic linear olefin is selected from the group consisting of (a) an olefin selected from the group consisting of hex-1-ene, hex-2-ene, 4-methylpent-1-ene, and 2-methylpent-1-ene, and (b) the mixture of an olefin of (a) with an olefin selected from the group consisting of propylene, but-1-ene, and pent-1-ene.

12. The process according to claim 11, wherein the aliphatic linear olefin is 4-methylpent-1-ene.

13. The process according to claim 11, wherein the aliphatic linear olefin is 2-methylpent-1-ene.

14. The process according to claim 11, wherein the aliphatic linear olefin is hex-1-ene.

15. The process according to claim 11, wherein the aliphatic linear olefin is hex-2-ene.

16. The process according to claim 11, wherein the aliphatic linear olefin is a mixture of hex-1-ene and but-1-ene.

17. The process of claim 10, wherein said layered clay is selected from the group consisting of montmorillonite, bentonite, beidellite, nontronite and hectorite.

18. The process according to claim 10, wherein said layered clay is selected from the group consisting of montmorillonite and bentonite.

19. The process according to claim 10, wherein said catalyst is selected from the group consisting of
hydrogen ion-exchanged bentonite,
aluminium ion-exchanged bentonite,
alumina pillared bentonite,
hydrogen ion-exchanged alumina pillared bentonite, and
aluminium ion-exchanged alumina pillared bentonite.

* * * * *